(12) United States Patent
Adams

(10) Patent No.: US 9,554,815 B2
(45) Date of Patent: Jan. 31, 2017

(54) SHOCKWAVE VALVULOPLASTY WITH MULTIPLE BALLOONS

(71) Applicant: SHOCKWAVE MEDICAL, INC., Fremont, CA (US)

(72) Inventor: John M. Adams, Snohomish, WA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 286 days.

(21) Appl. No.: 13/962,315

(22) Filed: Aug. 8, 2013

(65) Prior Publication Data

US 2014/0046353 A1  Feb. 13, 2014

Related U.S. Application Data

(60) Provisional application No. 61/681,068, filed on Aug. 8, 2012.

(51) Int. Cl.
*A61M 29/00* (2006.01)
*A61B 17/22* (2006.01)
*A61M 25/10* (2013.01)

(52) U.S. Cl.
CPC ... *A61B 17/22004* (2013.01); *A61B 17/22012* (2013.01); *A61B 17/22022* (2013.01);
(Continued)

(58) Field of Classification Search
CPC ............... A61B 17/22004; A61B 17/22012; A61B 17/2202; A61B 17/12136; A61B 17/12122; A61B 17/225; A61B 17/2251; A61B 17/2256; A61B 2017/22005; A61B 2017/22007; A61B 2017/22008; A61B 2017/22009; A61B 2017/22011; A61B 2017/22021; A61B 2017/22025; A61B 2017/22051; A61B 2017/22054; A61B 2017/22055; A61B 2017/22062; A61B 2017/22064; A61B 2017/22098; A61B 17/22022; A61B 17/2255; A61B 17/2258; A61B 2017/00783; A61B 8/12; A61M 2025/1086; A61M 25/1002; A61M 25/1011; A61M 25/104; A61M 2025/109; A61M 2025/1045; A61M 2025/1072; A61M 2025/1015; A61M 1/125; A61M 1/127; A61M 29/00; A61M 29/02
(Continued)

(56) References Cited

U.S. PATENT DOCUMENTS 3,413,976 A   12/1968   Voolfovich
3,902,499 A   9/1975    Shene
(Continued)

FOREIGN PATENT DOCUMENTS

CN   101043914 A   9/2007
DE   3038445 A1    5/1982
(Continued)

OTHER PUBLICATIONS

Extended European Search Report and Search Opinion received for European Patent Application No. 098253933, mailed on Feb. 28, 2013, 6 pages.
(Continued)

*Primary Examiner* — Katrina Stransky
*Assistant Examiner* — Katherine Schwiker
(74) *Attorney, Agent, or Firm* — Morrison & Foerster LLP

(57) ABSTRACT

Described herein are shock wave devices and methods for the treatment of calcified heart valves. One variation of a shock wave device includes three balloons that are each sized and shaped to fit within a concave portion of a valve cusp when inflated with a liquid and a shock wave source
(Continued)

within each of the three balloons. Each balloon is separately and/or independently inflatable, and each shock wave source is separately and/or independently controllable. Methods of treating calcified heart valves using a shock wave device can include advancing a shock wave device having one or more balloons and a shock wave source in each of the balloons to contact a heart valve, inflating the one or more balloons with a liquid such that the balloon is seated within a concave portion of a valve cusp, and activating the shock wave source.

13 Claims, 13 Drawing Sheets

(52) U.S. Cl.
CPC ............... *A61B 2017/22025* (2013.01); *A61B 2017/22055* (2013.01); *A61B 2017/22098* (2013.01); *A61M 25/1011* (2013.01); *A61M 29/00* (2013.01)

(58) Field of Classification Search
USPC .......... 606/128; 604/101.01, 101.03, 101.05; 600/439, 471, 16, 18
See application file for complete search history.

(56) References Cited

U.S. PATENT DOCUMENTS

| | | | |
|---|---|---|---|
| 4,027,674 A | 6/1977 | Tessler et al. | |
| 4,030,505 A | 6/1977 | Tessler | |
| 4,671,254 A | 6/1987 | Fair | |
| 4,809,682 A | 3/1989 | Forssmann et al. | |
| 4,878,495 A | 11/1989 | Grayzel | |
| 4,900,303 A | 2/1990 | Lemelson | |
| 5,046,503 A | 9/1991 | Schneiderman | |
| 5,057,106 A | 10/1991 | Kasevich et al. | |
| 5,154,722 A | 10/1992 | Filip et al. | |
| 5,195,508 A | 3/1993 | Muller et al. | |
| 5,245,988 A | 9/1993 | Einars et al. | |
| 5,295,958 A | 3/1994 | Shturman | |
| 5,368,591 A | 11/1994 | Lennox et al. | |
| 5,417,208 A | 5/1995 | Winkler | |
| 5,505,702 A | 4/1996 | Arney | |
| 5,582,578 A | 12/1996 | Zhong et al. | |
| 5,609,606 A | 3/1997 | O'Boyle | |
| 5,846,218 A | 12/1998 | Brisken et al. | |
| 5,931,805 A | 8/1999 | Brisken | |
| 6,113,560 A | 9/2000 | Simnacher | |
| 6,186,963 B1 | 2/2001 | Schwarze et al. | |
| 6,287,272 B1 | 9/2001 | Brisken et al. | |
| 6,352,535 B1 | 3/2002 | Lewis et al. | |
| 6,440,061 B1 | 8/2002 | Wenner et al. | |
| 6,652,547 B2 | 11/2003 | Rabiner et al. | |
| 6,689,089 B1 | 2/2004 | Tiedtke et al. | |
| 6,736,784 B1 | 5/2004 | Menne et al. | |
| 6,755,821 B1 | 6/2004 | Fry | |
| 7,618,432 B2 | 11/2009 | Pedersen et al. | |
| 7,803,168 B2 * | 9/2010 | Gifford .............. | A61B 17/2202 600/462 |
| 8,162,859 B2 | 4/2012 | Schultheiss et al. | |
| 8,556,813 B2 | 10/2013 | Cioanta et al. | |
| 8,574,247 B2 | 11/2013 | Adams et al. | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 9,044,618 B2 | 6/2015 | Hawkins et al. | |
| 2001/0044596 A1 | 11/2001 | Jaafar | |
| 2003/0004434 A1 | 1/2003 | Greco et al. | |
| 2003/0163081 A1 | 8/2003 | Constantz et al. | |
| 2003/0176873 A1 | 9/2003 | Chernenko et al. | |
| 2004/0044308 A1 | 3/2004 | Naimark et al. | |
| 2004/0082859 A1 | 4/2004 | Schaer | |
| 2004/0249401 A1 | 12/2004 | Rabiner et al. | |
| 2005/0075662 A1* | 4/2005 | Pedersen ................ | A61B 17/22 606/194 |
| 2005/0090846 A1 | 4/2005 | Pedersen et al. | |
| 2005/0171527 A1 | 8/2005 | Bhola | |
| 2005/0245866 A1 | 11/2005 | Azizi | |
| 2005/0251131 A1 | 11/2005 | Lesh | |
| 2006/0069385 A1* | 3/2006 | Lafontaine ............. | A61B 18/02 606/21 |
| 2006/0074484 A1 | 4/2006 | Huber | |
| 2006/0190022 A1 | 8/2006 | Beyar et al. | |
| 2007/0088380 A1 | 4/2007 | Hirszowicz et al. | |
| 2007/0129667 A1 | 6/2007 | Tiedtke et al. | |
| 2007/0299481 A1 | 12/2007 | Syed et al. | |
| 2008/0188913 A1 | 8/2008 | Stone et al. | |
| 2009/0030503 A1 | 1/2009 | Ho | |
| 2009/0041833 A1 | 2/2009 | Bettinger et al. | |
| 2009/0247945 A1 | 10/2009 | Levit et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0094209 A1 | 4/2010 | Drasler et al. | |
| 2010/0114020 A1 | 5/2010 | Hawkins et al. | |
| 2010/0179424 A1* | 7/2010 | Warnking et al. ............ | 600/437 |
| 2010/0324554 A1 | 12/2010 | Gifford et al. | |
| 2011/0034832 A1 | 2/2011 | Cioanta et al. | |
| 2011/0118634 A1 | 5/2011 | Golan | |
| 2011/0257523 A1 | 10/2011 | Hastings et al. | |
| 2012/0071889 A1 | 3/2012 | Mantell et al. | |
| 2012/0095461 A1 | 4/2012 | Herscher et al. | |
| 2012/0116289 A1 | 5/2012 | Hawkins et al. | |
| 2012/0143177 A1 | 6/2012 | Avitall | |
| 2012/0253358 A1* | 10/2012 | Golan ........................... | 606/128 |
| 2013/0116714 A1 | 5/2013 | Adams et al. | |
| 2013/0150874 A1 | 6/2013 | Kassab | |
| 2014/0039514 A1 | 2/2014 | Adams et al. | |
| 2014/0046229 A1 | 2/2014 | Hawkins et al. | |
| 2014/0052145 A1 | 2/2014 | Adams et al. | |
| 2014/0074111 A1 | 3/2014 | Hakala et al. | |
| 2014/0074113 A1 | 3/2014 | Hakala et al. | |
| 2014/0214061 A1 | 7/2014 | Adams et al. | |
| 2014/0243820 A1 | 8/2014 | Adams et al. | |
| 2014/0243847 A1 | 8/2014 | Hakala et al. | |
| 2014/0288570 A1 | 9/2014 | Adams | |
| 2015/0073430 A1 | 3/2015 | Hakala et al. | |
| 2015/0238208 A1 | 8/2015 | Adams et al. | |
| 2015/0320432 A1 | 11/2015 | Adams | |

FOREIGN PATENT DOCUMENTS

| | | |
|---|---|---|
| JP | 3-63059 A | 3/1991 |
| JP | 10-99444 A | 4/1998 |
| JP | 10-314177 A | 12/1998 |
| JP | 2004-357792 A | 12/2004 |
| JP | 2007-532182 A | 11/2007 |
| JP | 2008-506447 A | 3/2008 |
| JP | 2011-528963 A | 12/2011 |
| WO | 89/11307 A1 | 11/1989 |
| WO | 2005/099594 A1 | 10/2005 |
| WO | 2006/006169 A2 | 1/2006 |
| WO | 2007/088546 A2 | 8/2007 |
| WO | 2010/014515 A2 | 2/2010 |
| WO | 2010/014515 A3 | 8/2010 |
| WO | 2011/069025 A1 | 6/2011 |
| WO | 2013/059735 A1 | 4/2013 |
| WO | 2014/025620 A1 | 2/2014 |

OTHER PUBLICATIONS

Final Office Action received for U.S. Appl. No. 12/611,997, mailed on Dec. 11, 2012, 9 pages.
Final Office Action received for U.S. Appl. No. 12/611,997, mailed on Nov. 10, 2011, 15 pages.
Final Office Action received for U.S. Appl. No. 12/611,997, mailed on Oct. 24, 2013, 10 pages.
Non Final Office Action received for U.S. Appl. No. 12/611,997, mailed on Apr. 8, 2013, 9 pages.

(56) References Cited

OTHER PUBLICATIONS

Non Final Office Action received for U.S. Appl. No. 12/611,997, mailed on Aug. 24, 2012, 11 pages.
Non Final Office Action received for U.S. Appl. No. 12/611,997, mailed on Jun. 21, 2011, 13 pages.
Non-Final Office Action received for U.S. Appl. No. 12/611,997, mailed on Feb. 13, 2014, 9 pages.
Final Office Action received for U.S. Appl. No. 13/207,381, mailed on Nov. 2, 2012, 7 pages.
Final Office Action received for U.S. Appl. No. 13/207,381, mailed on Nov. 7, 2013, 7 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.
Non-Final Office Action received for U.S. Appl. No. 13/207,381, mailed on Feb. 25, 2014, 8 pages.
Non Final Office Action received for U.S. Appl. No. 13/232,730, mailed on Apr. 23, 2013, 10 pages.
Non Final Office Action received for U.S. Appl. No. 13/291,875 mailed on Feb. 28, 2013, 8 pages.
Notice of Allowance received for U.S. Appl. No. 13/291,875, mailed on Sep. 17, 2013, 11 pages.
Notice of Allowance received for U.S. Appl. No. 14/046,635, mailed on Dec. 17, 2013, 7 pages.
Office Action received for Australian Patent Application No. 2009313507, issued on Nov. 13, 2013, 3 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages of Official copy only.
Office Action received for Japanese Patent Application No. 2011-534914, mailed on Oct. 1, 2013, 5 pages (2 pages of English Translation and 3 pages of Official copy).
International Preliminary Report on Patentability received for PCT Patent Application No. PCT/US2009/063354, mailed on May 19, 2011, 6 pages.
International Search Report received for PCT Patent Application No. PCT/US2009/063354, mailed on Jun. 11, 2010, 3 pages.
International Written Opinion received for PCT Patent Application No. PCT/US2009/063354, mailed on Jun. 11, 2010, 4 pages.
International Preliminary Report on Patentability received for PCT Patent Application No. PCT/US2011/051606, issued on May 14, 2013, 6 pages.
International Search Report and Written Opinion received for PCT Patent Application No. PCT/US2011/051606, mailed on Apr. 24, 2012, 9 pages.
International Preliminary Report on Patentability received for PCT Patent Application No. PCT/US2012/063925, mailed on May 22, 2014, 12 pages.
International Search Report received for PCT Patent Application No. PCT/US2012/063925, mailed on Mar. 25, 2013, 3 pages.
International Search Report and Written Opinion received for PCT Patent Application No. PCT/US2013/054104, mailed on Oct. 22, 2013, 12 pages.
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Non Final Office Action received for U.S. Appl. No. 12/482,995, mailed on Aug. 13, 2014, 10 pages.
Notice of Allowance received for U.S. Appl. No. 12/482,995, mailed on Dec. 24, 2014, 6 pages.
Advisory Action Received for U.S. Appl. No. 12/581,295, mailed on Jul. 3, 2014, 3 pages.
Final Office Action received for U.S. Appl. No. 12/581,295, mailed on Jun. 5, 2014, 14 pages.

Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non Final Office Action received for U.S. Appl. No. 12/611,997, mailed on Nov. 26, 2014, 8 pages.
Notice of Allowance received for U.S. Appl. No. 12/611,997, mailed on Apr. 15, 2015, 7 pages.
Advisory Action Received for U.S. Appl. No. 13/049,199, mailed on Jun. 7, 2012, 3 pages.
Final Office Action received for U.S. Appl. No. 13/049,199, mailed on Aug. 11, 2014, 8 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Non Final Office Action received for U.S. Appl. No. 13/207,381, mailed on Nov. 25, 2014, 5 pages.
Notice of Allowance received for U.S. Appl. No. 13/207,381, mailed on Apr. 14, 2015, 7 pages.
Advisory Action received for U.S. Appl. No. 13/267,383, mailed on Jan. 6, 2014, 4 pages.
Final Office Action received for U.S. Appl. No. 13/267,383, mailed on Oct. 25, 2013, 8 pages.
Non-Final Office Action received for U.S. Appl. No. 13/267,383, mailed on Feb. 25, 2015, 9 pages.
Non Final Office Action received for U.S. Appl. No. 13/465,264, mailed on Oct. 29, 2014, 13 pages.
Non-Final Office Action received for U.S. Appl. No. 13/465,264, mailed on Dec. 23, 2014, 13 pages.
Notice of Allowance received for U.S. Appl. No. 13/465,264, mailed on May 8, 2015, 7 pages.
Final Office Action received for U.S. Appl. No. 13/646,570, mailed on Dec. 23, 2014, 10 pages.
Non Final Office Action received for U.S. Appl. No. 13/646,570, mailed on Oct. 29, 2014, 10 pages.
Notice of Allowance received for U.S. Appl. No. 13/646,570, mailed on Mar. 11, 2015, 7 pages.
Non-Final Office Action received for U.S. Appl. No. 13/646,583, mailed on Oct. 31, 2014, 8 pages.
Notice of Allowance received for U.S. Appl. No. 13/831,543, mailed on Oct. 8, 2014, 14 pages.
Notice of Allowance received for U.S. Appl. No. 13/957,276, mailed on Aug. 28, 2015, 9 pages.
Non Final Office Action received for U.S. Appl. No. 14/079,463, mailed on Mar. 4, 2014, 9 pages.
Notice of Allowance received for U.S. Appl. No. 14/079,463, mailed on Apr. 1, 2014, 5 pages.
Advisory Action received for U.S. Appl. No. 14/229,735, mailed on Nov. 3, 2015, 3 pages.
Final Office Action received for U.S. Appl. No. 14/229,735, mailed on Aug. 27, 2015, 7 pages.
Non Final Office Action received for U.S. Appl. No. 14/229,735, mailed on May 7, 2015, 8 pages.
Non-Final Office Action received for U.S. Appl. No. 14/271,276, mailed on Aug. 4, 2014, 7 pages.
Notice of Allowance received for U.S. Appl. No. 14/271,276, mailed on Feb. 25, 2015, 8 pages.
Final Office Action received for U.S. Appl. No. 14/271,342, mailed on Feb. 27, 2015, 7 pages.
Non-Final Office Action received for U.S. Appl. No. 14/271,342, mailed on Sep. 2, 2014, 6 pages.
Notice of Allowance received for U.S. Appl. No. 14/271,342, mailed on Mar. 13, 2015, 5 pages.
Notice of Allowance received for Canadian Patent Application No. 2,727,429, mailed on May 26, 2015, 1 page.
Office Action received for Canadian Patent Application No. 2,727,429, mailed on Apr. 14, 2015, 4 pages.
Notice of Acceptance Received for Australian Patent Application No. 2009257368, mailed on Aug. 28, 2014, 2 pages.
Notice of Acceptance Received for Australian Patent Application No. 2009313507, mailed on Nov. 17, 2014, 2 pages.

(56) References Cited

OTHER PUBLICATIONS

Decision to Grant received for Japanese Patent Application No. 2011-513694, mailed on Oct. 7, 2014, 3 pages (Official Copy only). (See Communication under 37 CFR § 1.98(a) (3)).
Office Action Received for Japanese Patent Application No. 2011-534914, mailed on Jan. 13, 2015, 9 pages (7 pages of English Translation and 2 pages of Official Copy).
Office Action Received for Japanese Patent Application No. 2011-534914, mailed on Jul. 15, 2014, 3 pages (1 page of English Translation and 2 pages of Official Copy).
Office Action Received for Japanese Patent Application No. 2014-158517, mailed on May 19, 2015, 5 pages (2 pages of English Translation and 3 pages of Official Copy).
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol, vol. 95, 2003, pp. 67-75.
Gambihler et al., "Permeabilization of the Plasma Membrane of LI210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Current Hypertension Reports, vol. 14, 2012, pp. 567-572.
Kodama et al., "Shock Wave-Mediated Molecular Delivery into Cells", Biochimica et Biophysica Acta, vol. 1542, 2002, pp. 186-194.
Lauer et al., "Shock wave Permeabilization as a New Gene Transfer Method", Gene Therapy, vol. 4, 1997, pp. 710-715.
International Preliminary Report on Patentability received for PCT Patent Application No. PCT/US2009/047070, mailed on Dec. 23, 2010, 7 pages.
Written Opinion received for PCT Patent Application No. PCT/US2009/047070, mailed on Jan. 19, 2010, 5 pages.
International Preliminary Report on Patentability received for PCT Patent Application No. PCT/US2012/023172, mailed on Aug. 15, 2013, 6 pages.
Written Opinion received for PCT Patent Application No. PCT/US2012/023172, mailed on Sep. 28, 2012, 4 pages.
Written Opinion received for PCT Patent Application No. PCT/US2012/063925, mailed on Mar. 25, 2013, 9 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987, issued on Nov. 20, 2014, 11 pages.
International Preliminary Report on Patentability received for PCT Patent Application No. PCT/US2013/048277, mailed on Jan. 8, 2015, 9 pages.
International Preliminary Report on Patentability received for PCT Patent Application No. PCT/US2013/053292, mailed on Feb. 19, 2015, 9 pages.
International Preliminary Report on Patentability received for PCT Patent Application No. PCT/US2013/055431, mailed on Feb. 26, 2015, 7 pages.
International Search Report and Written Opinion received for PCT Patent Application No. PCT/US2013/055431, mailed on Nov. 12, 2013, 9 pages.
International Preliminary Report on Patentability received for PCT Patent Application No. PCT/US2013/059533, mailed on Mar. 26, 2015, 10 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/060453, mailed on Jan. 21, 2016, 15 pages.
International Preliminary Report on Patentability received for PCT Patent Application No. PCT/US2013/054104, mailed on Feb. 19, 2015, 8 pages.

\* cited by examiner

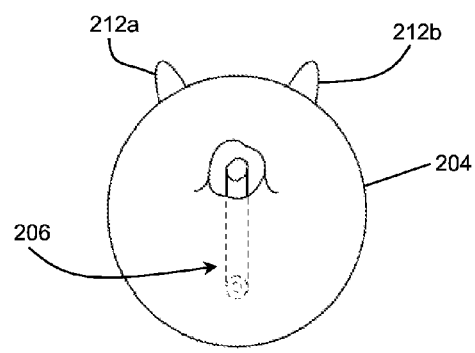
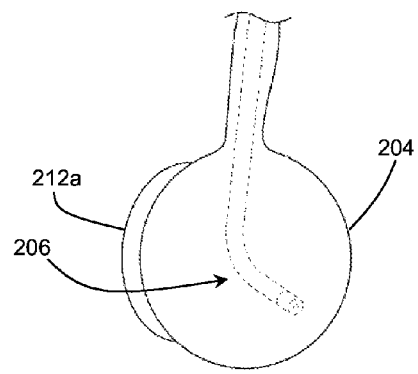
FIG. 2C  FIG. 2D
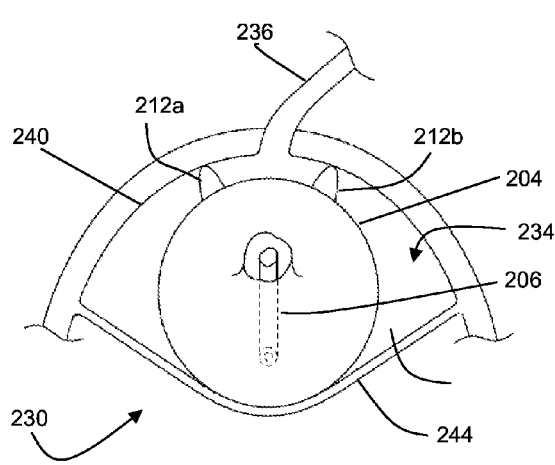
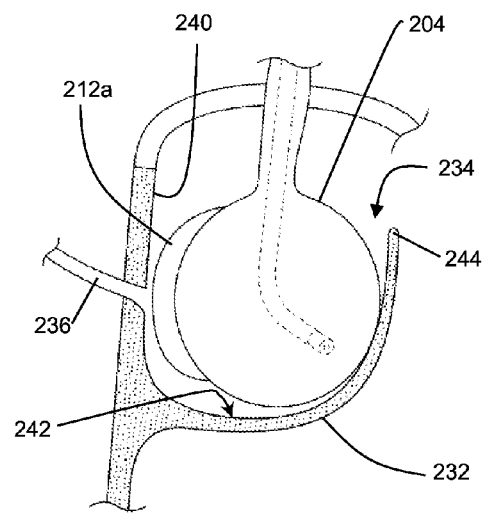
FIG. 2E  FIG. 2F

500 ⟶

| 502 | ADVANCE GUIDE CATHETER TO AORTIC VALVE IN A RETROGRADE DIRECTION |

| 504 | ADVANCE SHOCK WAVE DEVICE THROUGH GUIDE CATHETER |

| 506 | DEPLOY BALLOON FROM SHOCK WAVE DEVICE TO A FIRST CUSP |

| 508 | INFLATE BALLOON WITH A LIQUID |

| 510 | CONFIRM BALLOON IS SEATED WITHIN CONCAVE PORTION AND/OR SINUS OF THE FIRST CUSP |

| 512 | ACTIVATE SHOCK WAVE SOURCE TO TREAT FIRST CUSP |

| 514 | MOVE BALLOON TO A CONCAVE PORTION AND/OR SINUS OF A SECOND CUSP |

| 516 | ACTIVATE SHOCK WAVE SOURCE TO TREAT SECOND CUSP |

| 518 | MOVE BALLOON TO A CONCAVE PORTION AND/OR SINUS OF A THIRD CUSP |

| 520 | ACTIVATE SHOCK WAVE SOURCE TO TREAT THIRD CUSP |

| 552 | ADVANCE GUIDE CATHETER TO AORTIC VALVE IN A RETROGRADE DIRECTION |
|---|---|
| 554 | ADVANCE SHOCK WAVE DEVICE THROUGH GUIDE CATHETER |
| 556 | DEPLOY FIRST AND SECOND BALLOONS FROM SHOCK WAVE DEVICE TO FIRST AND SECOND CUSPS |
| 558 | INFLATE FIRST AND SECOND BALLOONS WITH A LIQUID SIMULTANEOUSLY |
| 560 | CONFIRM BALLOONS ARESEATED WITHIN CONCAVE PORTION AND/OR SINUS OF THE FIRST AND SECOND CUSPS |
| 562 | SIMULTANEOUSLY ACTIVATE SHOCK WAVE SOURCES IN FIRST AND SECOND BALLOONS TO TREAT FIRST AND SECOND CUSPS |
| 564 | DEFLATE AT LEAST ONE OF THE FIRST AND SECOND BALLOONS |
| 566 | INFLATE A BALLOON IN THIRD CUSP |
| 568 | CONFIRM BALLOON IS SEATED WITHIN CONCAVE PORTION AND/OR SINUS OF THE THIRD CUSP |
| 570 | ACTIVATE SHOCK WAVE SOURCE IN AT LEAST THE THIRD BALLOON TO TREAT THIRD CUSP |

FIG. 5C

SHOCKWAVE VALVULOPLASTY WITH MULTIPLE BALLOONS

CROSS-REFERENCE TO RELATED APPLICATIONS

This application claims the benefit of U.S. Provisional Application 61/681,068 filed on Aug. 8, 2012, which is hereby incorporated by reference in its entirety.

BACKGROUND

Aortic valve stenosis results in the narrowing of the aortic valve. Aortic valve stenosis may be exacerbated by a congenital defect where the aortic valve has one leaflet (unicuspid) or two leaflets (bicuspid) instead of three leaflets. In many cases, the narrowing of the valve is the result of aortic valve calcification, where calcified plaques accumulate on the leaflets and/or annulus of the aortic valve. For example, calcium plaques deposited on the cusps of the leaflets may stiffen the leaflets, thereby narrowing the valve opening and interfering with efficient blood flow across the valve.

Although research is underway in the development of a replacement aortic valve, one may prefer to soften the leaflets by cracking the calcium deposits on the native valve instead of replacing it with an artificial valve. Accordingly, improved methods of softening a calcified aortic valve may be desirable.

BRIEF SUMMARY

Described herein are shock wave devices and methods for the treatment of calcified heart valves. The application of shock waves to a calcified region of a valve may help to crack and/or break the calcium deposits, thereby softening and/or loosening and/or removing calcium deposits that stiffen the mechanical properties of the valve. Softening and/or loosening and/or removing calcium deposits may allow the valve to regain at least a portion of its normal function. One variation of a device may comprise at least one balloon that is sized and shaped to fit within a concave portion of a valve cusp when inflated with a liquid and a shock wave source within the balloon. Optionally, a device for treating a calcified heart valve may comprise three balloons that are each sized and shaped to fit within a concave portion of a valve cusp when inflated with a liquid and a shock wave source in each of the three balloons. Each balloon may be separately and/or independently inflatable, and each shock wave source may be separately and/or independently controllable. A shock wave device comprising three balloons and three shock wave sources may be used for treating a tricuspid valve, such as the pulmonary valve and the aortic valve. Shock wave devices comprising one or two balloons and one or two shock wave sources may be used for treating unicuspid, bicuspid and/or tricuspid valves.

Methods of treating calcified heart valves using a shock wave device may comprise advancing a shock wave device having one or more balloons and a shock wave source in each of the balloons to contact a heart valve, inflating the one or more balloons with a liquid such that the balloon is seated within a concave portion of a valve cusp, and activating the shock wave source. The mechanical force of the shock waves may act to crack and/or break calcium deposits located within the concave portion of the valve cusp. Inflation of the one or more balloons with a liquid may act to automatically align and/or seat the balloon within the concave portion of a valve cusp. Balloons and shock wave sources may be inflated and activated sequentially or simultaneously for the treatment of all the cusps of a valve. Once the desired level of treatment has been attained, the balloons may be deflated and withdrawn. Although the description below describes and depicts the treatment of an aortic valve, it should be understood that similar devices and methods may be used to treat any heart valve, e.g., the pulmonary valve, mitral valve, tricuspid valve, as may be desirable.

Other devices and methods that may be used to crack and/or break calcified deposits in an aortic valve (e.g., as part of a valvuloplasty procedure) are described in co-pending U.S. Pat. Pub. No. 2011/0295227 filed Aug. 10, 2011, U.S. Pat. Pub. No. 2013/0116714 filed Nov. 8, 2011, U.S. patent application Ser. No. 13/957,276 filed Aug. 1, 2013, which are hereby incorporated by reference in their entirety.

One variation of a device for the treatment of a heart valve (e.g., a heart valve having a plurality of cusps each having a concave portion) may comprise a first elongate body, a first balloon sealably enclosing a portion of the first elongate body, a first shock wave source coupled to the first elongate body and enclosed within the first balloon, a second elongate body, a second balloon sealably enclosing a portion of the second elongate body, and a second shock wave source coupled to the second elongate body and enclosed within the second balloon. The first and second balloons may be independently inflatable with a liquid and may be sized and shaped such that when inflated with the liquid, a portion of the balloons contact the valve. The portion of the balloons that contact the valve may approximate the size and shape of a concave portion of a valvular cusp. The device may optionally comprise a third elongate body, a third balloon sealably enclosing a portion of the third elongate body, and a third shock wave source coupled to the third elongate body and enclosed within the third balloon, where the third balloon may be independently inflatable with a liquid. In some variations, the shock wave source may be movable within their respective balloons. For example, the shock wave sources may be rotatable about a longitudinal axis of their respective elongate bodies, and/or may be advanceable along a longitudinal axis of their respective elongate bodies.

Another variation of a device for treating a heart valve (e.g., a heart valve having a plurality of cusps each having a concave portion) may comprise a first elongate body, a first balloon sealably enclosing a portion of the first elongate body, a first shock wave source coupled to the first elongate body and enclosed within the first balloon, a second elongate body, a second balloon sealably enclosing a portion of the second elongate body, a second shock wave source coupled to the second elongate body and enclosed within the second balloon, a third elongate body, a third balloon sealably enclosing a portion of the third elongate body, and a third shock wave source coupled to the third elongate body and enclosed within the third balloon. The first, second, and third balloons may be independently inflatable with a liquid and may be sized and shaped such that when inflated with the liquid, a portion of the balloons contact the valve. The portion of the balloons that contact the valve may approximate the size and shape of a concave portion of a valvular cusp.

Any of the devices described herein may further comprise at least one stand-off on the external surface of at least one of the balloons. In some variations, the at least one stand-off may comprise a curved ridge along a segment of the external surface of the balloon. Optionally, the elongate bodies of any of the devices described herein may comprise a compressed configuration and an expanded configuration, wherein in the compressed configuration, a distal portion of the elongate bodies may be relatively straight and in the expanded configuration, the distal portion of the elongate bodies may be curved.

Also described herein are methods for applying shock waves to an aortic valve. One variation of a method may comprise introducing shock wave device into a patient's vasculature, where the shock wave device may comprise a first elongate body, a first balloon sealably enclosing a portion of the first elongate body, a first shock wave source coupled to the first elongate body and enclosed within the first balloon, a second elongate body, a second balloon sealably enclosing a portion of the second elongate body, and a second shock wave source coupled to the second elongate body and enclosed within the second balloon, advancing the shock wave device within the vasculature to contact an aortic valve having a first cusp and a second cusp, inflating the first balloon with a liquid, where inflating the first balloon causes the first balloon to be aligned within a concave portion of the first cusp, and activating the first shock wave source to apply a shock wave to the first cusp. The first and second balloons may be independently inflatable with a liquid. The shock wave device may be advanced in a retrograde direction in the vasculature. In some variations, the method may further comprise inflating the second balloon with a liquid, where inflating the second balloon causes the second balloon to be aligned within a concave portion of the second cusp, confirming that the first balloon and the second balloon are each aligned within the concave portions of the first and second cusp respectively, and deflating the second balloon before activating the first shock wave source.

Optionally, some methods may comprise deflating the first balloon after activating the first shock wave source, inflating the second balloon with a liquid, where inflating the second balloon causes the second balloon to be aligned within a concave portion of the second cusp, and activating the second shock wave source to apply a shock wave to the second cusp. Alternatively or additionally, a method may comprise inflating the second balloon with a liquid, where inflating the second balloon causes the second balloon to be aligned within a concave portion of the second cusp, confirming that the first balloon and the second balloon are each aligned within the concave portions of the first and second cusp respectively, and activating the second shock wave source to apply a shock wave to the second cusp. In some variations, the first and second shock wave sources may be activated substantially simultaneously. These methods may be used to apply shock waves to a first cusp and a second cusp, where the first cusp is a right semilunar cusp and the second cusp is a posterior semilunar cusp, or the first cusp is a left semilunar cusp and the second cusp is a posterior semilunar cusp, or the first cusp is a right semilunar cusp and the second cusp is a left semilunar cusp. Shock waves may be applied to the first and second cusps simultaneously or sequentially. Optionally, the shock wave devices used in any of these methods may comprise a third elongate body, a third balloon sealably enclosing a portion of the third elongate body, and a third shock wave source coupled to the third elongate body and enclosed within the third balloon, where the third balloon is independently inflatable with a liquid.

Another variation of a method for applying shock waves to an aortic valve may comprise introducing shock wave device into a patient's vasculature, the shock wave device comprising a first elongate body, a first balloon sealably enclosing a portion of the first elongate body, a first shock wave source coupled to the first elongate body and enclosed within the first balloon, advancing the shock wave device within the vasculature to contact an aortic valve having a first cusp and a second cusp, inflating the first balloon with a liquid, where inflating the first balloon causes the first balloon to be aligned within a concave portion of only the first cusp, and treating the first cusp by activating the first shock wave source to apply a shock wave to the first cusp. The first and second balloons may be independently inflatable with a liquid. The shock wave device may be advanced in a retrograde direction in the vasculature. The method may further comprise deflating the first balloon after treating the first cusp, moving the first balloon to the second cusp, inflating the first balloon with a liquid, where inflating the first balloon causes the first balloon to be aligned within a concave portion of only the second cusp, and treating the second cusp by activating the first shock wave source to apply a shock wave to the second cusp. In some variations, the shock wave device may further comprise a second elongate body, a second balloon sealably enclosing a portion of the second elongate body, a second shock wave source coupled to the second elongate body and enclosed within the second balloon. The second balloon may be inflatable with a liquid independently from the first balloon. A method using a shock wave device comprising two balloons may optionally comprise deflating the first balloon after treating the first cusp, inflating the second balloon with a liquid, where inflating the second balloon causes the second balloon to be aligned within a concave portion of only the second cusp, and treating the second cusp by activating the second shock wave source to apply a shock wave to the second cusp. Optionally, a shock wave device used in any of the methods described herein may further comprise at least one stand-off on the external surface of at least one of the balloons such that when the at least one balloon is inflated with a liquid and is located with a concave portion of a cusp, the balloon does not obstruct blood flow to a coronary artery.

BRIEF DESCRIPTION OF THE DRAWINGS

FIG. 2C depicts a proximal view of the distal portion of FIG. 2B. FIG. 2D is a side view of the distal portion of FIG. 2B. FIG. 2E is a top view of the device of FIGS. 2A-2D deployed within a cusp of an aortic valve. FIG. 2F is a side view of the device of FIGS. 2A-2D deployed within a cusp of an aortic valve.

FIGS. 5A-5C are flowchart representations of additional variations of methods for treating a calcified heart valve using a shock wave device.

DETAILED DESCRIPTION

Figure 1A:
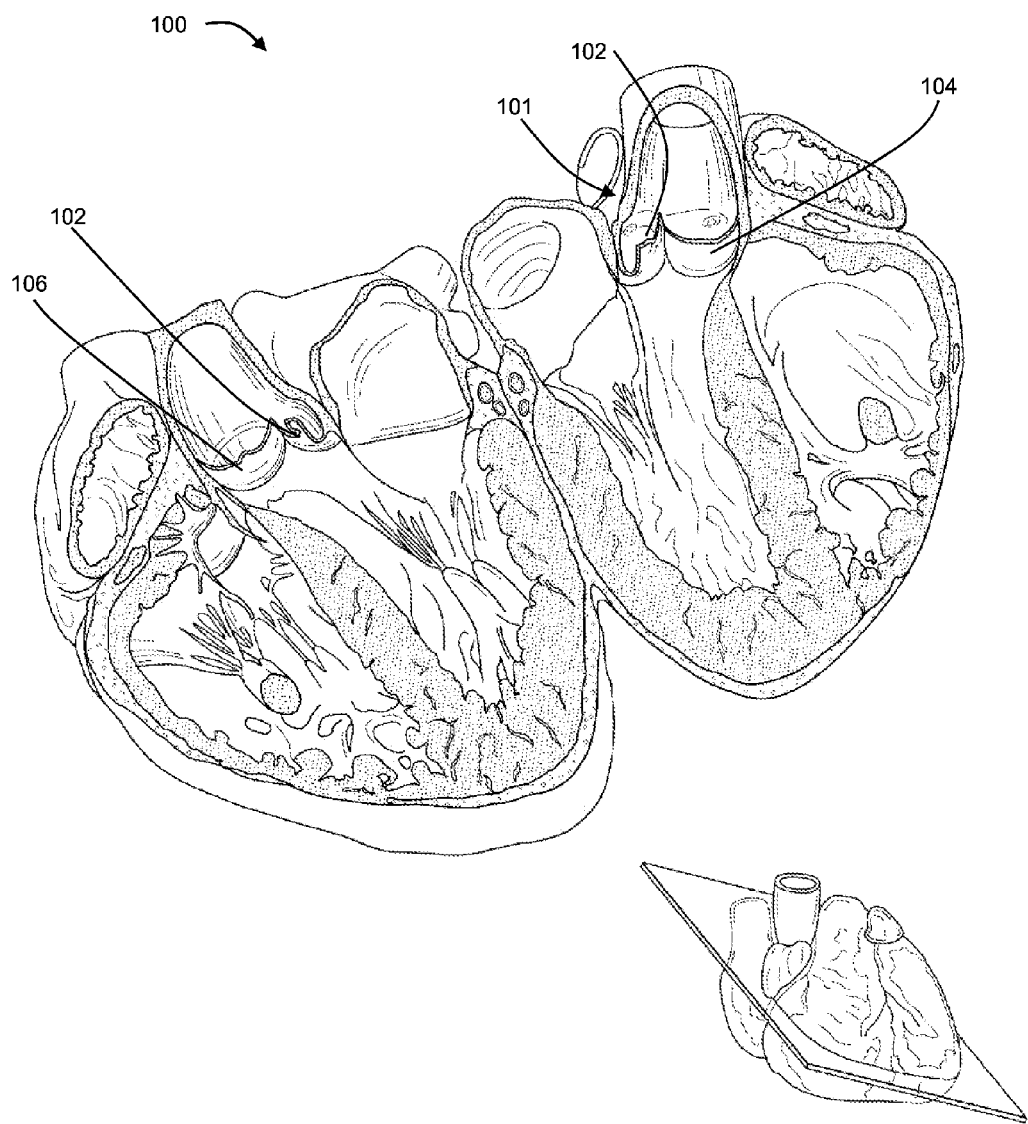
FIG. 1A depicts a cutaway view of the heart (sectioned along the plane indicated in the inset.
Figure 1B:
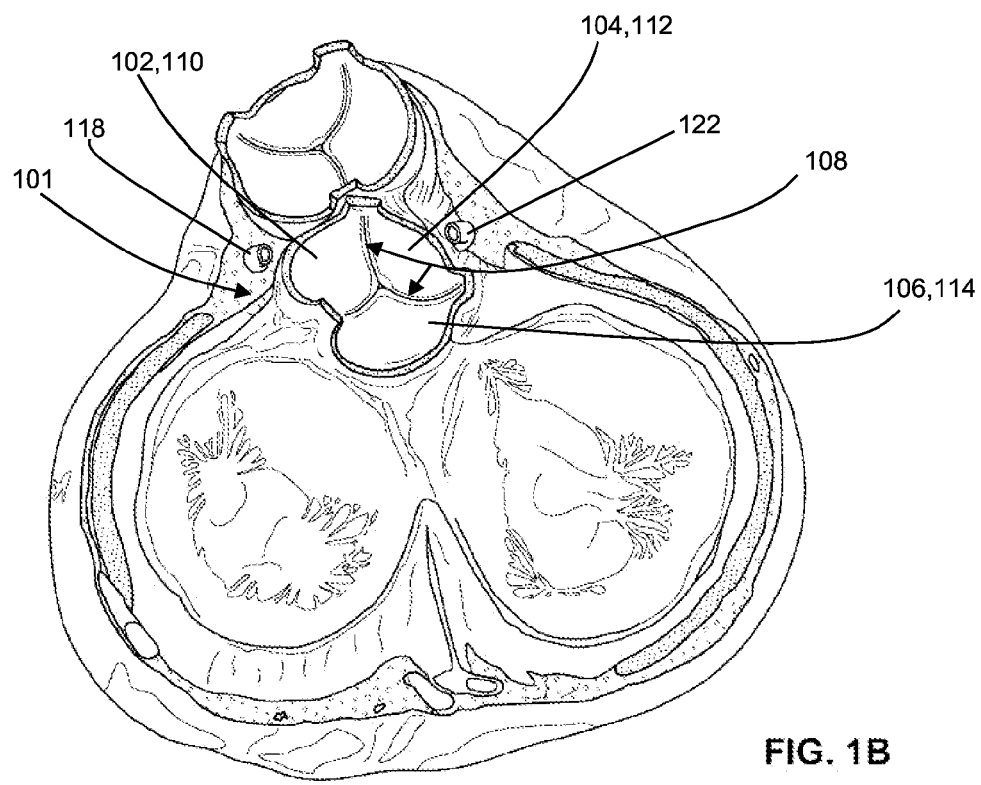
FIG. 1B depicts a top view of the heart, as viewed from the base with the atria removed.
Figure 1C:
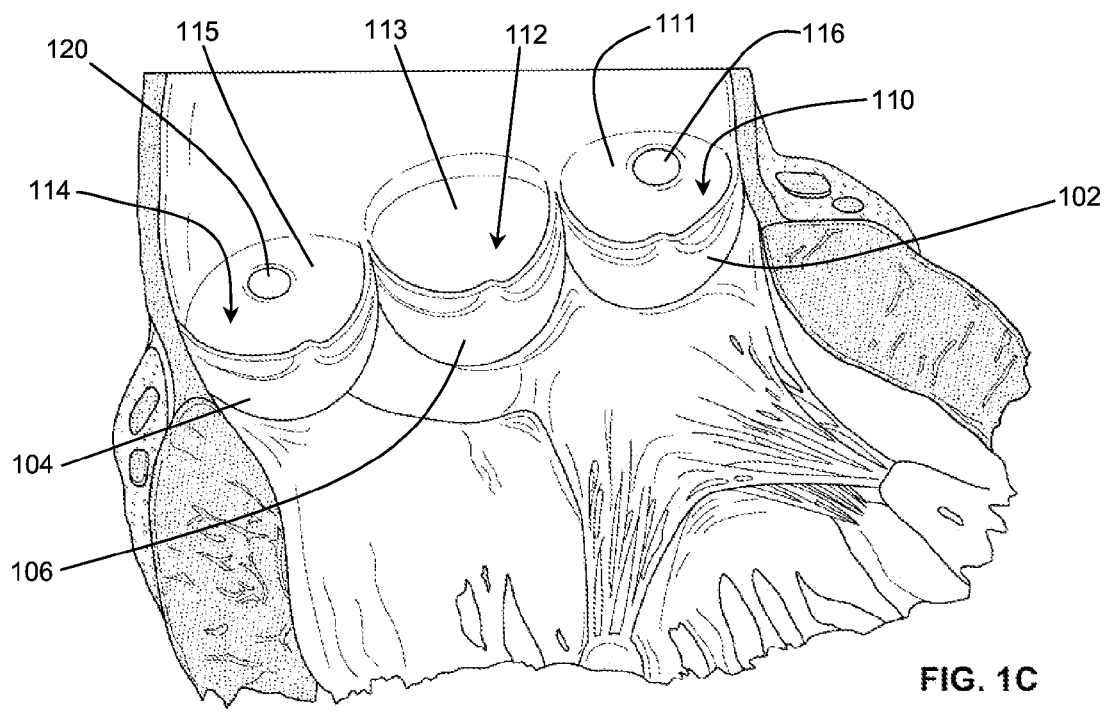
FIG. 1C is a view of the aortic valve that has been cut anteriorly between the left cusp and the right cusp and splayed open.

FIGS. 1A-1C depict various views of the valves of the heart. FIG. 1A is a cross-sectional view of a heart 100 taken along the plane indicated by the inset. The aortic valve 101 comprises a left semilunar leaflet or cusp 102, a right semilunar leaflet or cusp 104 and a posterior semilunar leaflet or cusp 106. Each cusp has a free margin, which articulates with the free margins of the other cusps when the valve closes, and an attached margin that attaches the cusp in a semilunar fashion to the aortic wall. When the aortic valve is closed, the ventricular side of the cusps may have a convex surface and the aortic side of the cusps may have a concave surface. The concave portion of each of the cusps may be bordered by the concave surface of the cusp, the free margin of the cusp, the attached margin of the cusp, and may also include a portion of the valve wall. Alternatively or additionally, the concave portion of each of the cusps may include the aortic sinus associated with each cusp. FIG. 1B depicts a top view (viewed from the base with the atria removed) of the aortic valve 101 in a closed configuration, showing the concave portion of each of the left semilunar cusp 102, right semilunar cusp 104 and posterior semilunar cusp 106. As illustrated there, the free margins 108 of each of the cusps articulate with each other to prevent the blood from passing through the valve when closed. The concave portions 110, 112, 114 of the left, right, and posterior cusps respectively are also shown in FIG. 1B. As depicted in FIG. 1C, the concave portions of each cusp may also include a portion of the aortic sinus 111, 113, 115 associated with that cusp. The concave portion 110 or aortic sinus 111 of the left cusp 102 may comprise an opening 116 to the left coronary artery 118, and the concave portion 112 or aortic sinus 113 of the right cusp 104 may comprise an opening 120 to the right coronary artery 122. The concave portion 114 or aortic sinus 115 of the posterior cusp may not have any coronary artery openings.

Figure 1D:
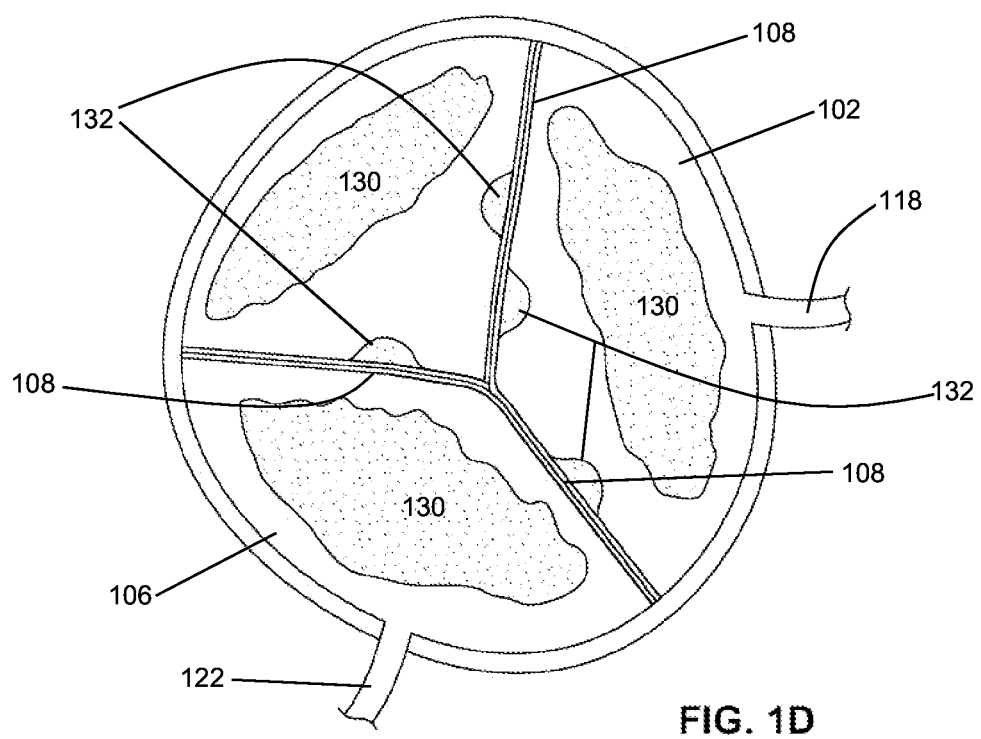
FIG. 1D is a top view of a calcified aortic valve.
Figure 1E:
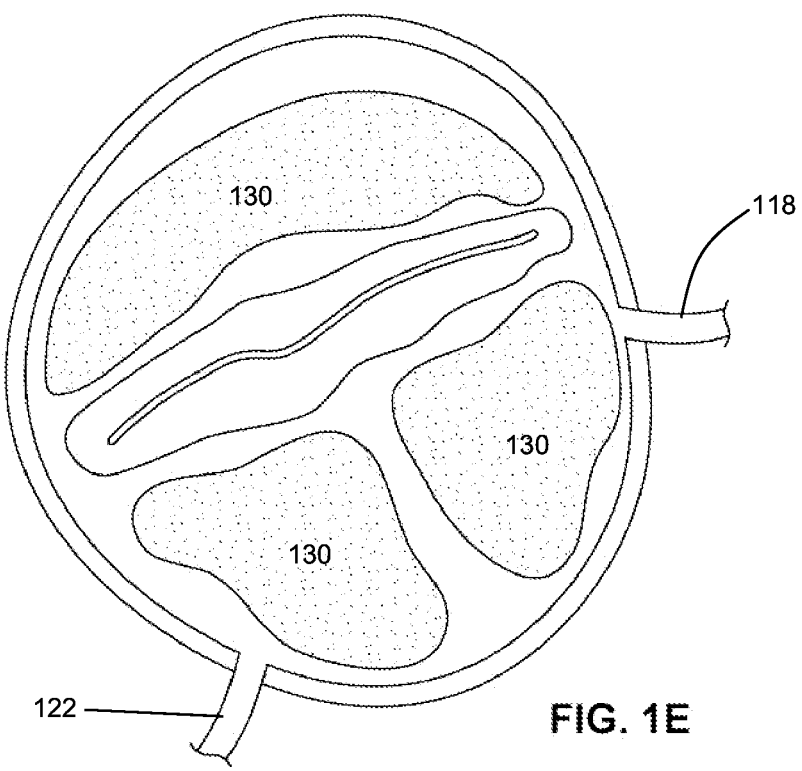
FIG. 1E is a top view of a bicuspid aortic valve.
Figure 2A:
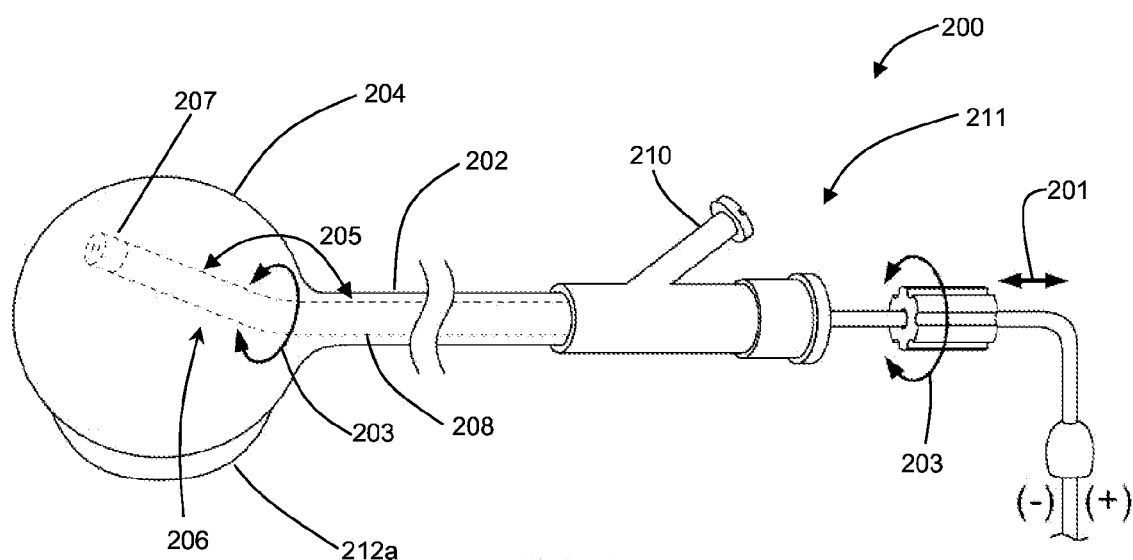
FIG. 2A schematically depicts one variation of a shock wave device for the treatment of calcified heart valves.
Figure 2B:
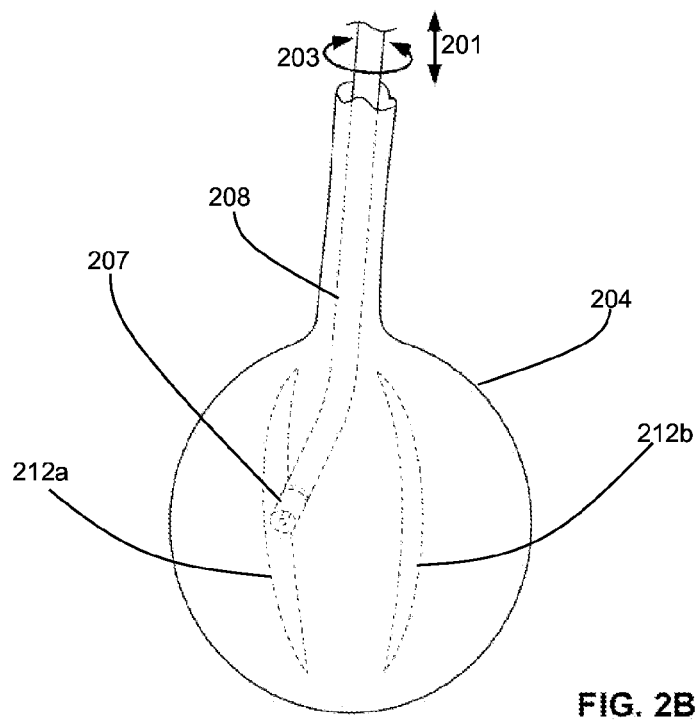
FIG. 2B depicts a distal portion of the shock wave device of FIG. 2A.

FIGS. 1D and 1E depict aortic valves that may be susceptible to stenosis. As shown in FIG. 1D, calcified plaques or deposits may accumulate on the aortic side of the leaflets, for example, along the concave portion of the cusp, as indicated by the dashed areas 130, 132. Calcium deposits on the aortic valve leaflets and walls may stiffen the valve considerably, and compromise its ability to open and close effectively. Nodular deposits 132 may accumulate along the free margins of the leaflets, and sheets of deposits 130 may accumulate within the concave portion of the leaflets (e.g., along the aortic side of the leaflets). Nodular deposits 132 may act to adhere the free margins of the cusps to each other, which would reduce the size of the valve opening. Sheet-like deposits along the aortic surface of the cusp (e.g., the concave portion and/or aortic sinus) may act to stiffen the cusp and interfere with its ability to open and close. Some patients may have a bicuspid aortic valve, which is a congenital condition that may result in an aortic valve having two leaflets instead of three leaflets. FIG. 1E depicts a bicuspid aortic valve, the function of which may be particularly compromised by the accumulation of calcified deposits along the free margins and/or concave portions of the two leaflets. Cracking, breaking and/or removing these deposits may help the aortic valve to regain its normal function. The shock wave devices and methods described herein may be delivered to the concave portions of the aortic valve leaflets and/or aortic sinuses in order to crack, break, soften, remove and/or otherwise reduce the effect of calcium deposits on the function of the valve.

A shock wave device that may be used to treat calcified regions of the aortic valve may comprise an elongate body, a balloon that sealably encloses a distal portion of the elongate body, and a shock wave source coupled to the elongate body and enclosed within the balloon. The balloon may be filled with a liquid, and when the shock wave source is activated, shock waves may propagate through the liquid and apply a mechanical force on the wall of the balloon. By placing the balloon wall in contact with a calcified tissue region (e.g., concave portion of a cusp and/or aortic sinus), the mechanical force from the shock wave may be transferred to the calcium deposit, thereby cracking and/or breaking the deposit. The closer the contact between the balloon wall and the calcified tissue, the more efficient the transfer of mechanical energy from the shock wave device to the calcium deposits. Furthermore, the closer the shock wave source within the balloon is to the calcified tissue, the greater the magnitude of mechanical force that may be delivered to the calcium deposit. The size and shape of the balloon may be selected so that when the balloon is inflated with a liquid, at least a portion of the balloon is capable of being seated and/or positioned within the concave portion and/or aortic sinus of a cusp. For example, the balloon may be sized and shaped such that when the balloon is inflated in the proximity of an aortic valve cusp, the balloon automatically seats and/or positions itself within the concave portion and/or sinus of the cusp. The size and shape of the balloon may be tailored to the unique geometry of a patient's aortic valve (e.g., to match the geometry of the aortic cusps and/or aortic sinus). For example, the diameter of a balloon may be from about 5 mm to about 15 mm, which may correspond to the size of a concave portion of a cusp. Balloons may be spherical, but may also have other shapes that may help to position it in a concave portion of a valve (e.g., tetrahedron with rounded and/or sharp corners or edges, pyramid with rounded and/or sharp corners or edges, square-circle-triangle block, etc.). The balloons may be made of a non-compliant material and may be molded to mimic the shape of a coronary sinus of the valve.

Optionally, the elongate body of the shock wave device may have shape memory such that it may be advanced through the vasculature in a relative straight configuration (e.g., constrained by a guide tube) and when deployed, may assume a curved or bent configuration that may help seat the balloon within (or in close proximity to) the aortic surface of the cusp prior to or during inflation. For example, the elongate body may be biased to assume a bent and/or an expanded configuration when deployed at or near a valve cusp, which may help the device to self-align the balloons within the concave portion and/or sinus of the cusp. The balloon may be bonded to a distal portion of the elongate body, which may provide a fluid path to fill the balloon with saline or saline/contrast mixture. The elongate body may be formed of a compliant material to absorb the volume changes that may be caused by the steam bubble that may arise from shock waves generated in the balloon. In some variations, the shock wave source enclosed within the balloon may be movable within the balloon, such that shock waves can be initiated from any location within the balloon to apply mechanical forces to a targeted region of tissue. For example, the shock wave source may be advanced or retracted longitudinally along the axis of the elongate body (e.g., in a proximal to distal direction), rotated (e.g., around the axis of the elongate body), and/or bent at an angle with respect to the axis of the elongate body (e.g., the shock wave source may be located at a distal tip of a steerable catheter and/or a catheter with shape memory such that it assumes a bent configuration when unconstrained).

Optionally, the balloon of a shock wave device may comprise one or more stand-off structures on its external surface. Examples of stand-off structures may include, but are not limited to, ridges, bumps, protrusions, struts, etc. These stand-off structures may help to keep an inflated balloon that is seated within the concave portion and/or sinus of a cusp from blocking any arterial openings that may be in the sinus. For example, having one or more stand-off structures on balloons that have been inflated in the left cusp or right cusp may help to prevent the balloon from blocking the openings of the left or right coronary arteries. Maintaining patency of the coronary artery openings may allow continuous perfusion to the heart while the shock wave procedure is being performed, which may help reduce the occurrence of cardiac ischemia during the procedure.

A shock wave device that comprises a single elongate body, balloon and shock wave source may be used to treat one cusp of a valve at a time (i.e., after treatment of a first cusp, the device may be repositioned and seated in a concave portion of a second cusp to treat the second cusp, and so on). In some variations, a shock wave device may comprise two or three sets of elongate bodies, balloons and shock wave sources, which may allow for the treatment of multiple cusps simultaneously, as well as for the treatment of bicuspid aortic valves. Additional balloons may also help to seat and/or position the shock wave device within the concave portion of the valve cusps more efficiently and/or precisely. While certain features and structures are described for particular variations of shock wave devices, it should be understood that those features and structures may also be incorporated into other variations of shock wave devices.

One variation of a shock wave device that may be used to crack and/or break calcified deposits located in the aortic valve is depicted in FIGS. 2A-2D. Shock wave device 200 may comprise an elongate body 202, a balloon 204 sealably enclosing a portion of the elongate body, and a shock wave source 206 within the balloon. The balloon 204 may be located at the distal end of the elongate body 202, and may be inflatable by the introduction of fluid (e.g., liquid) at the proximal end of the elongate body (e.g., via a port 210, which may be a luer lock connector of a proximal handle portion 211). Alternatively, the elongate body may have a separate fluid lumen for inflating the balloon. The balloon 204 may comprise two elongated protrusions or ridges 212a, 212b along its external surface, which may act as stand-offs to prevent occlusion of coronary artery openings when the balloon is inflated in a sinus of a cusp. The shock wave source 206 may comprise a shaft 208 and at least one electrode pair 207 located at the distal end of the shaft which are connected to a high voltage power supply. The shock wave source 206 may be advanced along the longitudinal axis of the elongate body 202 (e.g., into and out of the elongate body 202, according to arrows 201), and/or may be rotated around the longitudinal axis of the elongate body 202 (e.g., according to arrows 203, and/or may be bent at an angle) by turning and/or pushing and/or pulling a knob 213 of the proximal handle portion 211. The shaft 208 may be a steerable shaft where an actuating mechanism (e.g., pull wires) may be used to cause the shaft to bend, and/or may have shape memory, where the shaft is pre-shaped to have a bend 205 when in an unconstrained configuration. While the shock wave source 206 depicted in the drawings comprises an electrode pair 207 in a coaxial configuration at the distal tip of the shaft 208, it should be understood that there may be more than one electrode pair along the shaft, and that the electrode pair may have a variety of configurations. In some variations, the shock wave electrode pair may be located along a side of the shaft 208. Examples of shock wave electrode configurations are described in U.S. Pub. No. 2009/0312768 filed Jun. 11, 2009 and U.S. application Ser. No. 13/831,543 filed Mar. 14, 2013, which are both hereby incorporated by reference in their entirety. Alternatively or additionally, a shock wave source may comprise optical fibers or lasers that are configured to generate shock waves.

FIGS. 2C and 2D depict top and side views of the balloon 204, ridges 212a and 212b, and shock wave source 206. FIG. 2E depicts a top view and FIG. 2F depicts a side view of the shock wave device deployed at the aortic valve 230 (only the left cusp 232 of the valve is depicted). As seen from the side view in FIG. 2F, the balloon 204 is inflated with a liquid and is seated within a concave portion 234 of the left cusp 232. Inflation of the balloon 204 and/or shape memory of the elongate body 202 may help the balloon 204 to self-align into the concave portion 234 of the left cusp 232. The balloon may be seated within the concave portion 234 of the cusp such that the balloon is bordered by the valve wall 240 (e.g., wall of the sinus), the concave surface 242 (on the aortic side) of the cusp, and the free edge 244 of the cusp. When seated within the concave portion of a cusp, the balloon may be pressed against the valve wall 240 such that the balloon does not cross the free edge of the cusp and intersect with the free edge of another cusp (e.g., the balloon does not span across two cusps, and/or the balloon does not extend within the aortic valve orifice). As seen from the top view in FIG. 2E, the balloon is seated within the concave portion 234 such that it is bordered by the valve wall 240 and the free edge 244 of the cusp. The balloon may also comprise ridges 212a, 212b help to ensure that the balloon does not obstruct the opening 236 of the left coronary artery. While two ridges are depicted, it should be understood that there may be any number of ridges or protrusions as may be desirable for ensuring that there is a space between the balloon wall and the aortic wall (e.g., 1, 2, 3, 4, 5, 6, 8, 10, 12, 15, etc. protrusions or ridges).

Figure 3:
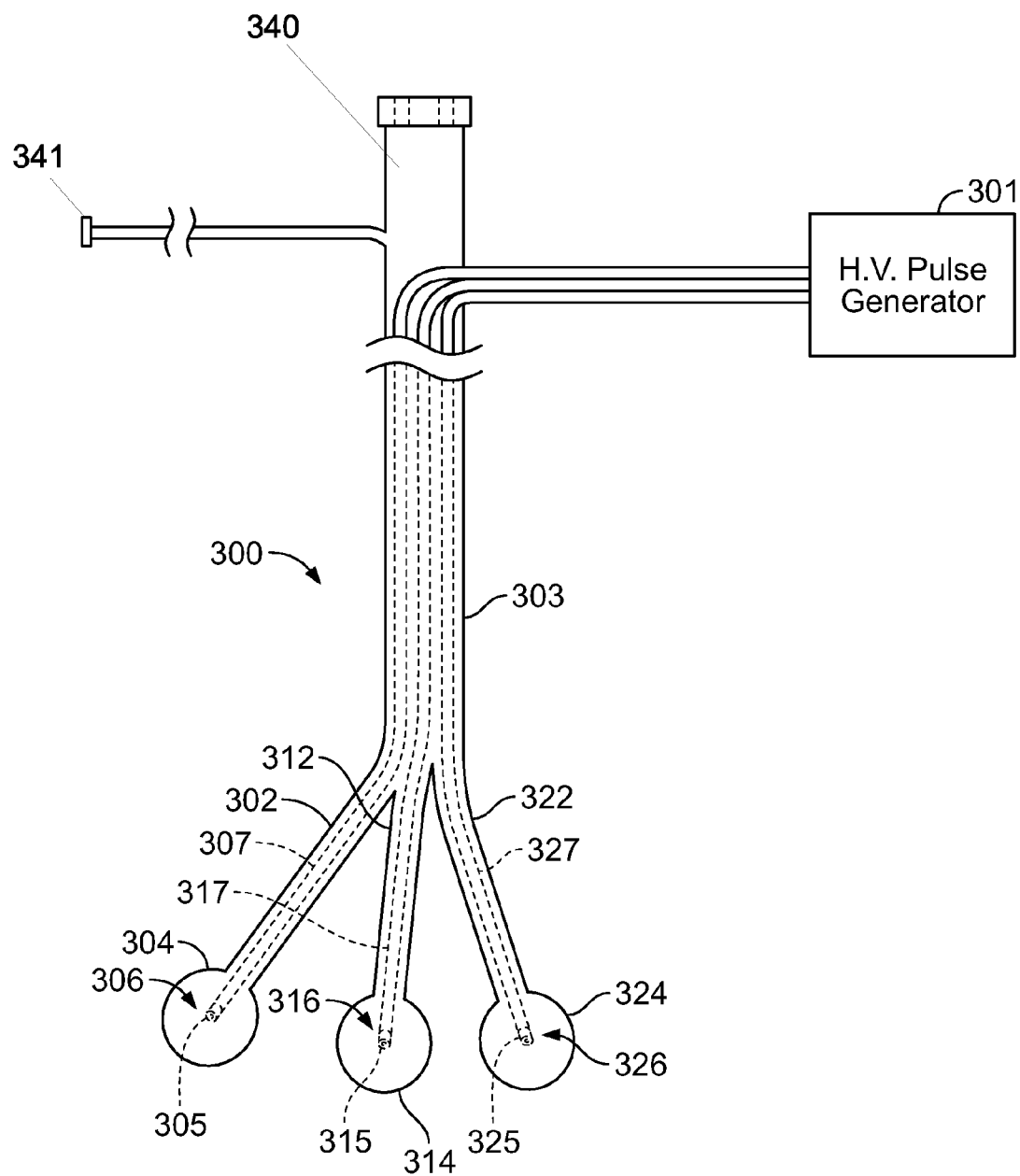
FIG. 3 schematically depicts one variation of a shock wave device for the treatment of calcified heart valves comprising three balloons and three shock wave sources within the balloon.

A shock wave device for the treatment of calcified heart valves may comprise additional sets of elongate bodies, balloons, and shock wave devices. Some variations may have two elongate bodies, two balloons (each of which sealably encloses a portion of one of the two elongate bodies), and two shock wave sources (one in each of the two balloons). Other variations may have three sets of elongate bodies, balloons, and shock wave devices, such as the shock wave device 300 depicted in FIG. 3. The shock wave device 300 may comprise a first elongate body 302, a first balloon 304 sealably enclosing a portion of the first elongate body, a first shock wave source 306, a second elongate body 312, a second balloon 314 sealably enclosing a portion of the second elongate body, a second shock wave source 316, a third elongate body 322, a third balloon 324 sealably enclosing a portion of the third elongate body, and a third shock wave source 326. The shock wave sources may be connected at a proximal end to a high voltage pulse generator 301, where a positive terminal of each shock wave source may be connected to a positive port of the pulse generator and a negative terminal of each shock wave source may be connected to a common ground terminal. The first, second and third balloons may be separately and/or independently inflatable (e.g., have separate inflation lumens). In some variations, the first, second and third balloons may be inflated one at a time (e.g., sequentially), and/or two at a time. All the balloons of a shock wave device may also be inflated simultaneously. For example, as depicted in FIG. 3, the three elongate bodies 302, 312, 322 connect to a common shaft 303, and share a common inflation lumen 341 of a proximal handle 340. The first, second and third shock wave sources may be separately and/or independently activated. Each of the shock wave sources 306, 316, 326 may comprise an insulating shaft 307, 317, 327 which may house the wiring between the high voltage pulse generator and the shock wave electrodes 305, 315, 325 at the distal end of the shaft. The pulse generator may be controlled by a controller that is programmed to provide voltage pulses to each of the shock wave sources sequentially (e.g., one at a time) or simultaneously (e.g., two at a time, three at a time). Each of the three balloons and corresponding shock wave sources may be inflated, actuated, and activated by three separate proximal handle portions, each similar to the handle portion described and depicted in FIG. 2A. Additional fluid ports and/or actuating mechanism for moving the shock wave source may be included at a proximal portion as may be desirable.

The insulating shafts 307, 317, 327 and/or the elongate bodies 302, 312, 322 may have be biased to expand when unconstrained (e.g., by an overtube or catheter). In some variations, the shafts and/or elongate bodies may be spring-biased, and/or may have shape memory such that when unconstrained, they assume a bent and/or expanded configuration. Expansion and/or bending of the shafts and/or elongate bodies may help to position the balloons along the aortic valve such that when inflated, the balloons may self-align with the cusps and may be seated and/or positioned within a concave portion of the cusp and/or the sinus of the cusp.

Figure 4A:
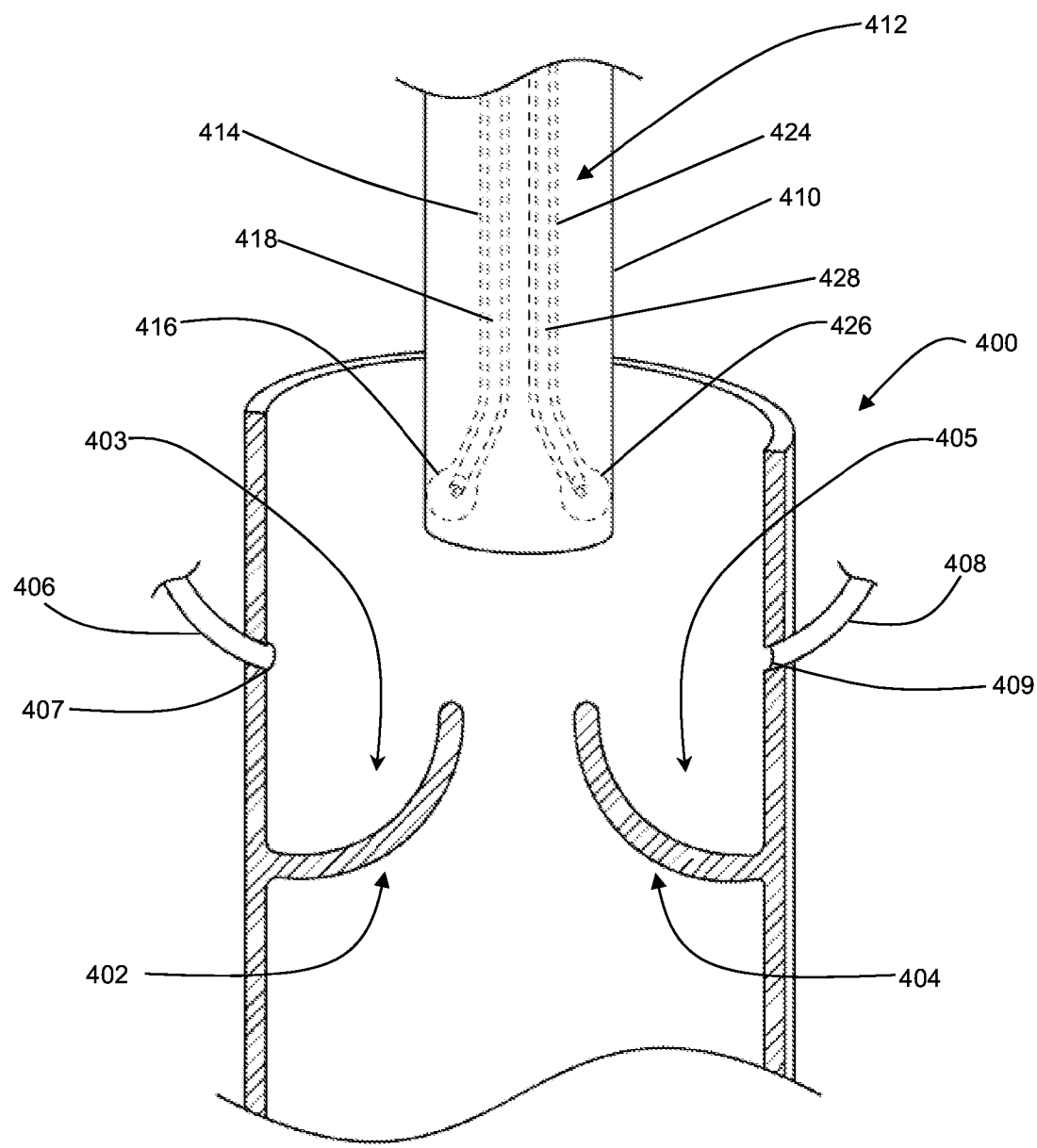
FIGS. 4A-4C depict one variation of method for treating a calcified heart valve using a shock wave device.
Figure 4B:
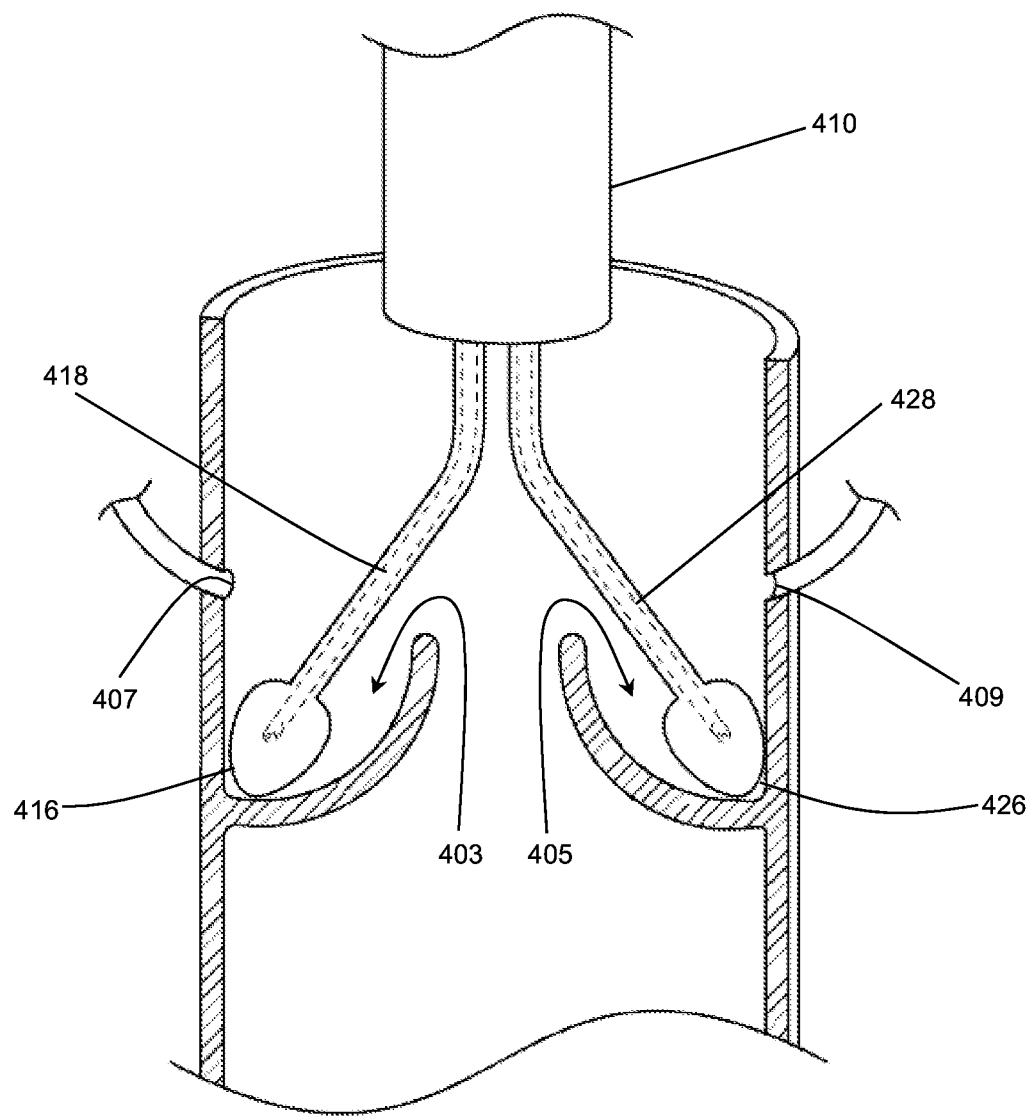
Figure 4C:
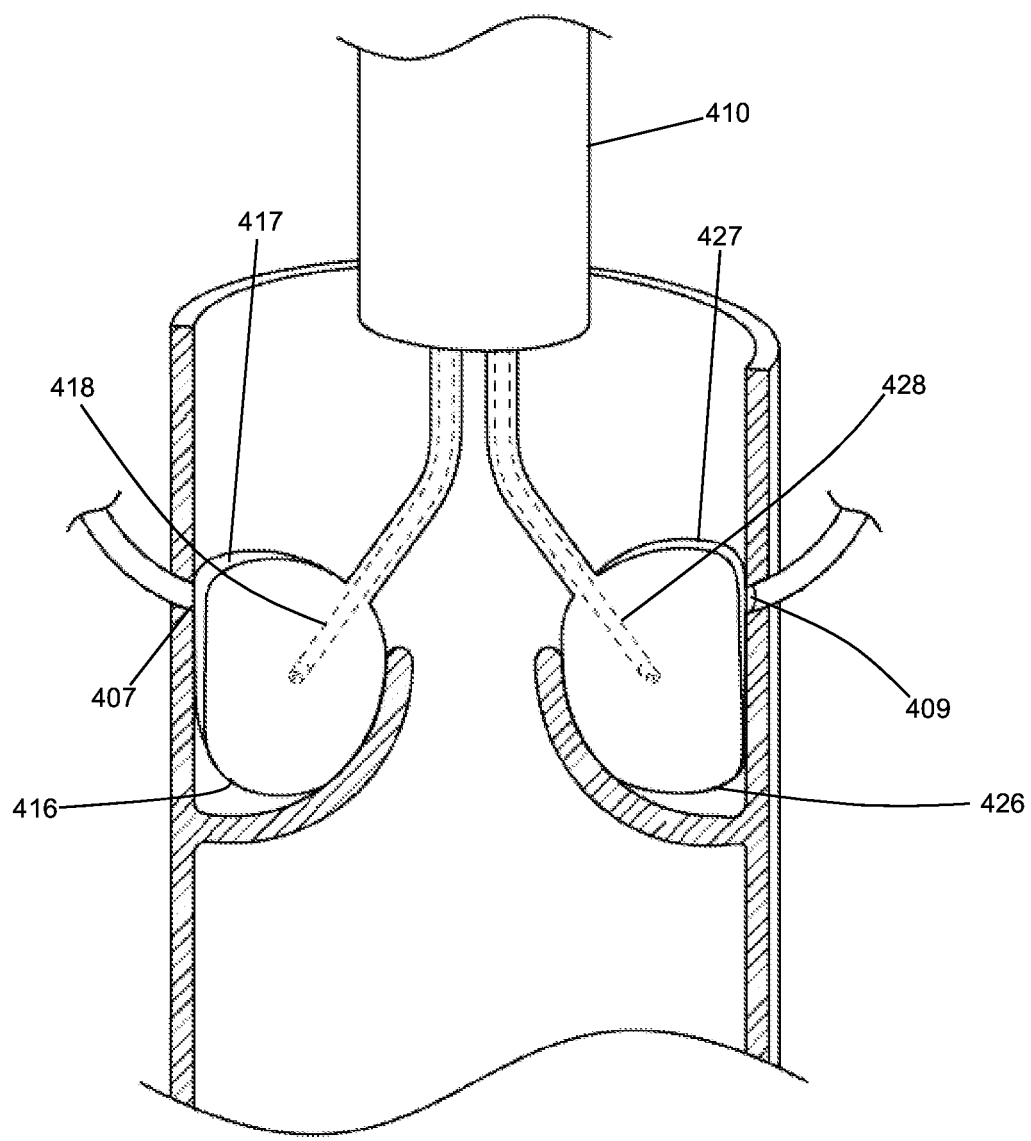

FIGS. 4A-4C depict one variation of a method for treating a calcified heart valve (e.g., an aortic valve) using a shock wave device. Although the method depicted there uses a shock wave device comprising two balloons, it should be understood that this method may be performed using any of the shock wave devices disclosed herein (e.g., shock wave devices having one balloon or three balloons). FIG. 4A depicts a cross-sectional schematic view of an aortic valve 400 with the left cusp 402 and the right cusp 404 (the posterior cusp is not shown for the sake of simplicity). The concave portion 403 of the left cusp 402 includes the left sinus and the opening 407 of the left coronary artery 406. The concave portion 405 of the right cusp 404 includes the right sinus and the opening 409 of the right coronary artery 408. A guide catheter 410 may be introduced into the vasculature and advanced in a retrograde direction (e.g., via a femoral artery) to the aortic valve 400. The guide catheter 410 (as well as any of components of the shock wave device) may comprise a radiopaque band or marker so that the location of the catheter may be determined using fluoroscopy. Alternatively or additionally, the location of the catheter and/or any shock wave devices may be determined using ultrasound. The guide catheter 410 may be positioned just downstream (e.g., above) from the cusps. A shock wave device 412 may then be advanced through the guide catheter 410 to the aortic valve. The shock wave device 412 may comprise a first elongate body 414, a first balloon 416 sealably attached to the distal end of the first elongate body 414, a first shock wave source 418 enclosed within the first balloon 416, a second elongate body 424, a second balloon 426 sealably attached to the distal end of the second elongate body 424, and a second shock wave source 428 enclosed within the second balloon 426. Alternatively, the shock wave device may be any of the shock wave devices described herein. The first and second elongate bodies and/or the shafts of the first and second shock wave sources may be biased such that they bend at an angle and/or expand when unconstrained. The shock wave device 412 may be advanced through the guide catheter 410 in a compressed configuration, where the first and second elongate bodies and/or the shafts of the first and second shock wave sources may be generally aligned with the longitudinal axis of the guide catheter 410.

As shown in FIG. 4B, advancing the shock wave device 412 distally beyond the distal end of the guide catheter may allow the first and second elongate bodies and/or the shafts of the first and second shock wave sources to assume their bent configuration, thereby expanding the shock wave device such that the first and second balloons 416, 426 (deflated during delivery) contact the aortic valve wall. The expansion of the shock wave device may at least partially align the balloons with the concave portions 403, 405 of the left and right cusps, and help to position the balloons away from the valve orifice and along the valve wall. Next, as depicted in FIG. 4C, one or both of the balloons may be inflated with a liquid, which may cause the balloons to self-align within the concave portions of the cusps, and may help reduce the amount of maneuvering of the shock wave device needed to position the balloons within the concave portions and/or sinuses of the cusps. In some variations, only one balloon may be inflated at a time, or two balloons may be inflated simultaneously. Inflating fewer balloons than the number of cusps of a valve may allow blood to flow through at least a portion of the valve, which may help to reduce the risk of an ischemic incident during the procedure.

Figure 4D:
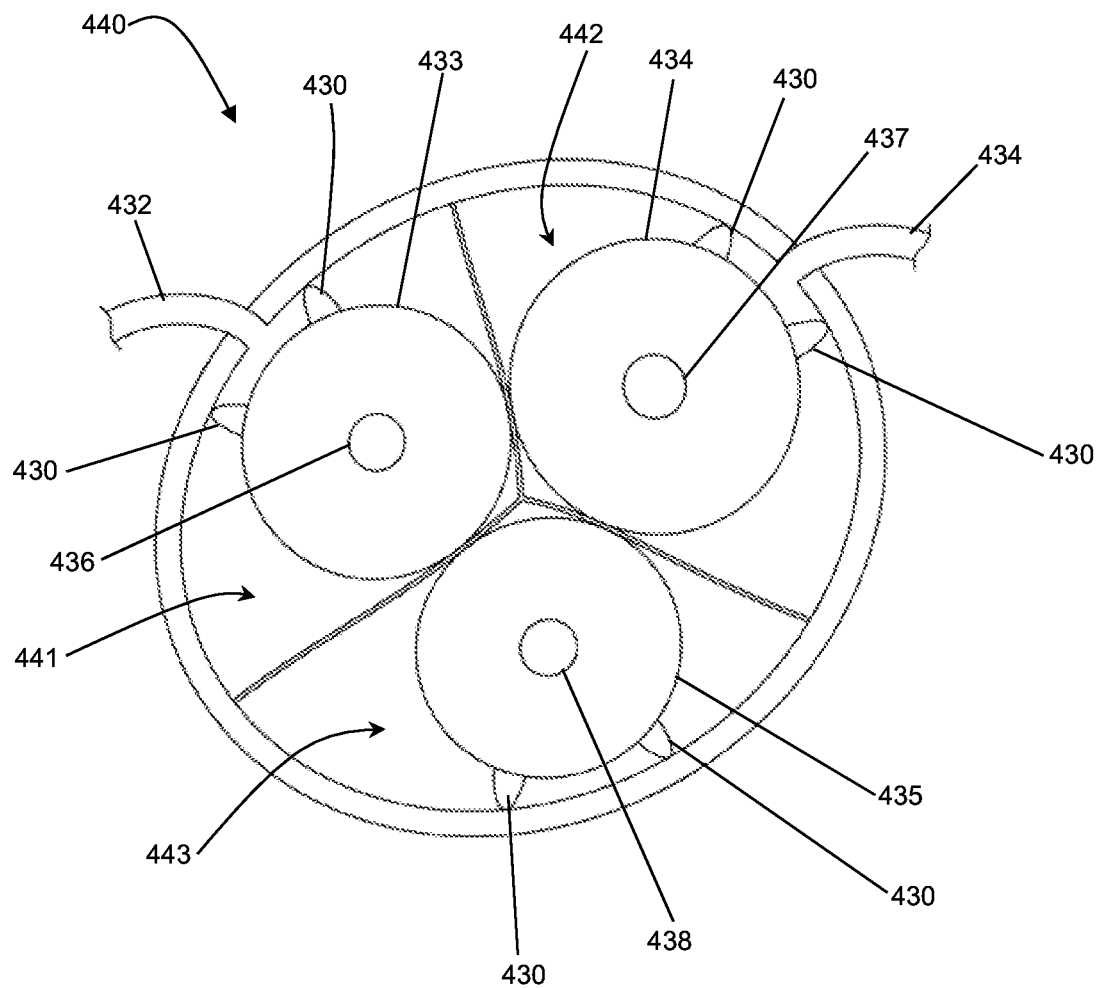
FIG. 4D depicts a schematic top view of a shock wave device deployed in an aortic valve.

The balloons may comprise one or more ridges 417, 427 (not shown in FIGS. 4A and 4B, but shown in FIG. 4C) that may act to maintain a space between the inflated balloon and the valve wall (e.g., such that the inflated balloon does not block the artery openings 407, 409). This may allow for continuous perfusion through the valve and around the cusps, as well as blood flow into the left and right coronary arteries 406, 408 through the artery openings 407, 409. FIG. 4D depicts a top view of a shock wave device comprising three balloons 433, 434, 435 (inflated with a fluid) enclosing three shock wave sources 436, 437, 438 that may be deployed to an aortic valve 440. Each balloon may comprise at least two ridges 430 that help to maintain a space between the balloon and the valve wall, which may help to prevent obstruction of the openings to the coronary arteries 432, 434. As seen there, each of the three balloons is seated within a concave portion and/or sinus 441, 442, 443 of each of the cusps of the aortic valve. The location of the balloons may be determined based on fluoroscopy and/or ultrasound, as previously indicated. For example, a portion of the ridges 417, 427 may be made of a radiopaque material that may be visualized using fluoroscopy. A radiopaque ridge may allow a practitioner to confirm that the balloons are seated within a concave portion and/or sinus of the cusps, as well as to confirm that the ridges themselves are not obstructing the openings to the coronary arteries and/or confirm that the balloons are not inserted through and/or obstructing the valve orifice. In some variations, the bias of the elongate body and/or shock wave shaft, along with inflation of the balloons may help to self-align the balloons with the concave portions of the cusps and/or automatically seat the balloons within the concave portions of the cusps. Such bias may also help to ensure that none of the balloons obstruct and/or extend through the valve orifice, but are instead pressed along the wall of the valve.

After a practitioner confirms that the balloons are located in the desired position, one or more of the shock wave sources may be activated to produce shock waves. The location of the balloons and/or shock wave devices may be monitored throughout the treatment procedure as needed to confirm that the balloons are in close proximity to and/or in contact with calcified regions of the valve. The mechanical force from the shock waves may propagate through the liquid to apply a mechanical force on any calcified deposit along the surface of the cusp. A plurality of shock waves may be applied to the cusps and/or other valve structures. In some variations, the shock wave devices may be moved within a balloon so that the mechanical forces from the shock waves may be focused on different areas of a cusp without moving the balloon. For example, shock wave treatment of a calcified cusp may comprise initiating shock waves from the shock wave source at a first location (which may, for example, apply mechanical force to calcified deposits along the attached edge of the cusp), then moving the shock wave source in the balloon to a second location, and then initiating shock waves from the shock wave source at a second location (which may, for example, focus the mechanical force to calcified deposits along the free edge of the cusp). Efficacy of the treatment may be subsequently evaluated based on imaging techniques (e.g., fluoroscopy and/or ultrasound) and/or physiological parameters. Examples of techniques that may be used to evaluate the efficacy of the treatment may include, but are not limited to, visual observation by ultrasound of leaflet activity (e.g., leaflet opening and closing) when the balloons are deflated or withdrawn from the valve, measuring ejection fraction, Duke Activity Status Index (DASI), peak velocity, peak gradient, valve effective orifice area, Doppler velocity, etc.

Optionally, after a desired amount of the calcium deposits have been cracked and/or loosened, and/or the leaflets of the valve have been softened, a transcatheter aortic valve implantation (TAVI) procedure may be performed. Cracking and/or breaking the calcium deposits on an aortic valve may help to improve the outcome of a subsequent TAVI procedure. Described below are additional methods that may comprise one or more of the steps described above.

Figure 5B:
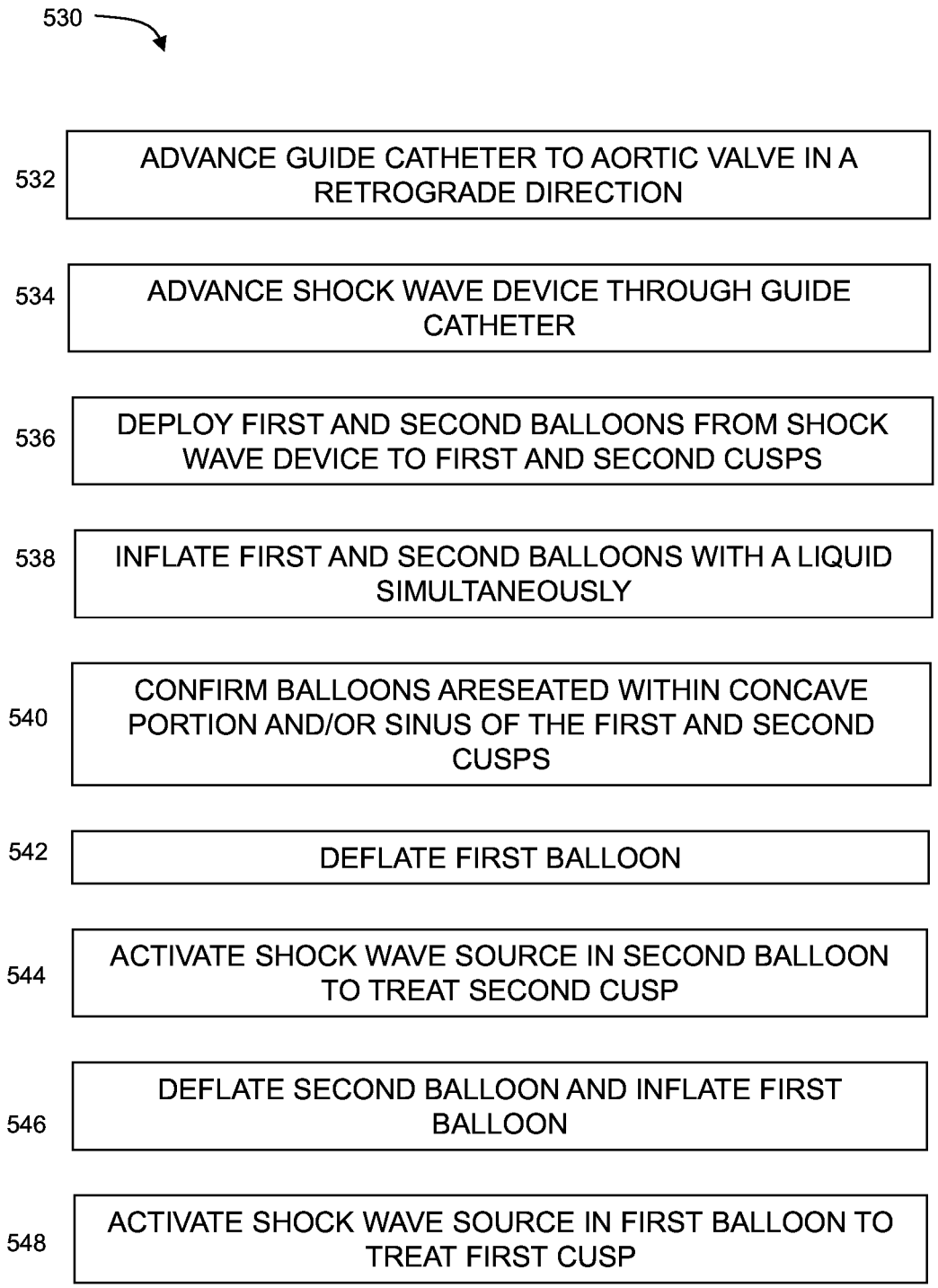

In some methods, a single cusp of a valve may be treated at a time, while in other methods, two or more cusps of a valve may be treated simultaneously. FIGS. 5A-5C depicts flowchart diagrams representing variations of methods for cracking and/or breaking calcified deposits that may be located along the surface of a cusp on the aorta side. In one variation, such as is depicted in FIG. 5A, a shock wave device with a single balloon and shock wave source within the balloon may be used to treat a first calcified cusp (e.g., the right cusp), then a second calcified cusp (e.g., the left cusp) and then a calcified third cusp (e.g., the posterior cusp) sequentially. In this method 500, a guide catheter is advanced in a retrograde direction to the aortic valve (502) and the shock wave device is advanced through the guide catheter (504), as previously described. A balloon is deployed to a first cusp (506), where it is inflated with a fluid (508), and its position within the concave portion and/or sinus of the cusp is confirmed (510). The shock wave source within the balloon may be activated (512) and the mechanical force from plurality of shock waves may act to crack and/or break the calcium deposits within the first cusp. Once that first cusp has been satisfactorily treated, the shock wave device may be moved (e.g., rotated), such that the balloon is moved from the first cusp to the concave portion of a second cusp (step 514) the balloon may or may not be deflated prior to moving it to the second cup). After the position of the balloon in the concave portion of the second cusp has been confirmed, the shock wave source within the balloon may be activated (516). The process may then be repeated for the third cusp (steps 518-520).

In another variation, as shown in FIG. 5B, a shock wave device with two balloons and two shock wave sources may be used to sequentially treat one calcified cusp at a time. In such a method 530, the shock wave device is advanced to the aortic valve, as previously described (steps 532, 534), and then both balloons may be deployed (536) and inflated simultaneously to seat the balloons within the concave portion of the cusps (538). Optionally, a shock wave device with three balloons and three shock wave sources may have all three balloons inflated simultaneously. Once the balloon positions have been confirmed (step 540, e.g., the balloons are aligned with the concave portions of the cusps, and/or are located within the cusps), a first balloon in a first cusp may be deflated while a second balloon in a second cusp may remain inflated (542). Where a three-balloon shock wave device is used, a third balloon in a third cusp may be deflated. The shock wave source in the second balloon may be activated to crack and/or break the calcified deposits within the second cusp (544). Inflating more than one balloon may be helpful to position and/or seat the balloons within the concave portion of a cusp. Deflating all but one of the balloons during treatment may help to reduce the obstruction of blood flow through the valve during a procedure, thus extending the time available to perform the whole procedure. After the second cusp has been treated, the second balloon may be deflated and the first balloon inflated for treating the first cusp (546). The shock wave source in the first balloon may be activated to crack and/or break the calcified deposits within the first cusp (548). These steps may be repeated as may be desirable (e.g., for the treatment of a third cusp, and/or repeated treatment of the first and second cusps).

FIG. 5C depicts an example of a method 550 for treating two (or three) calcified cusps simultaneously. A shock wave device comprising two balloons and two corresponding shock wave sources may be advanced to the aortic valve, as described previously (steps 552, 554). In some variations, a three-balloon shock wave device instead of a two-balloon shock wave device. Two balloons may be deployed (556) inflated simultaneously (558) to seat the balloons within the concave portion of the cusps (with a three-balloon device, the third balloon may optionally be inflated). Once the position of the balloons within the concave portions of the cusp and in desired contact with the calcified deposits have been confirmed (560), the two shock wave sources within the two balloons may be activated simultaneously to apply mechanical forces to the calcified deposits in both cusps (562). After the two cusps have been treated, at least one of the balloons may be deflated (564). The third cusp may be treated by rotating the shock wave device so that a balloon is aligned with and/or seated within the third cusp (e.g., in the case of a two-balloon shock wave system), inflating the balloon within the third cusp (566), confirming its location within the third cusp (568) and activating the shock wave source within that balloon to treat the third cusp (570). Where a three-balloon shock wave device is used, the device need not be re-positioned to treat the third cusp, and instead, the third balloon may be inflated (566), to seat it within the third cusp and the third shock wave source may be activated (570). Confirming the position of the third balloon within the third cusp may be optional. Optionally, when the third balloon is inflated, one or both of the other two balloons may be deflated. In some variations, three balloons may be inflated simultaneously to treat three cusps simultaneously. While a three balloon system may be capable of inflating more than one balloon to treat more than one cusp at a time, in some variations, a three balloon system may be used to treat a single cusp at a time (i.e., inflating only one balloon at a time). Sequential inflation of a single balloon at a time may be desirable in cases where a practitioner desires to reduce the level of obstruction of the aortic valve orifice during treatment.

In methods where two calcified cusps are treated simultaneously, one of the cusps may have a coronary artery opening in its sinus (e.g., a right or left cusp) while the other cusp may not have a coronary artery opening in its sinus (e.g., the posterior cusp). Leaving the third cusp (e.g., the left or right cusp) unobstructed by a balloon while the other two cusps are undergoing treatment may help ensure a consistent flow of blood to the coronary artery associated with that cusp, as well as to keep a portion of the valve orifice open during treatment. For example, balloons may be inflated in the left cusp and the posterior (non-coronary) cusp to treat those cusps, while the balloon aligned and/or positioned within the concave portion of the right cusp may remain deflated. After the left cusp has been treated, its corresponding balloon may be deflated and the balloon in the right cusp may be inflated. The shock wave source in the balloon in the right cusp may then be activated to treat the right cusp. Optionally, the balloon within the posterior cusp may remain inflated for continued treatment (e.g., simultaneously with treatment of the right cusp), or the balloon may be deflated. These steps may be repeated as desired. In other variations, the right and left cusps may be treated simultaneously, where the balloons seated in those cusps are inflated at the same time. As described previously, balloons may have one or more stand-off structures (e.g., ridges and the like) which may help to maintain a space between the balloon and the wall of the coronary sinus where the openings of the coronary arteries are located. Maintaining this space may allow blood to continue to flow to the coronary arteries and reduce the degree to which the inflated balloons obstruct the openings of the coronary arteries. After the left and right cusps have been treated, one or both of the balloons in the right and left cusps may be deflated and the balloon in the posterior cusp may be inflated. In still other variations, balloons may be seated and inflated in the three cusps of the aortic valve so that the three cusps may be treated simultaneously.

The methods and devices described above may also be used for the treatment of bicuspid aortic valves. For example, a method for treating a calcified bicuspid aortic valve may comprise inflating only one balloon of a shock wave device to treat only one cusp at a time. In other variations, methods for treating a calcified bicuspid aortic valve may comprise inflating two balloons at a time for simultaneous shock wave treatment of both of the cusps. Optionally, a TAVI procedure may be performed after treating the valve with the shock wave device.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed as new and desired to be protected by Letters Patent of the United States is:

1. A method for applying shock waves to an aortic valve having a first cusp and a second cusp each having a free edge comprising:
   introducing a shock wave device into a patient's vasculature, the shock wave device comprising a first elongate body, a first balloon sealably enclosing a portion of the first elongate body, a first shock wave source coupled to the first elongate body and enclosed within the first balloon, a second elongate body, a second balloon sealably enclosing a portion of the second elongate body, and a second shock wave source coupled to the second elongate body and enclosed within the second balloon, wherein the first and second balloons are independently inflatable with a liquid;
   advancing the shock wave device within the vasculature to the aortic valve;
   inflating the first balloon with a liquid, wherein inflating the first balloon causes the first balloon to be aligned within a concave portion of the first cusp facing the aorta;
   inflating the second balloon with a liquid, wherein inflating the second balloon causes the second balloon to be aligned within a concave portion of the second cusp facing the aorta and wherein the first and second balloons do not extend beyond the free edges of the first and second cusps respectively to permit blood to flow through the aortic valve; and
   activating the first shock wave source to apply a shock wave to the first cusp.

2. The method of claim 1, further comprising:
   after inflating the second balloon with a liquid and before activating the first shock wave source, confirming that the first balloon and the second balloon are each aligned within the concave portions of the first and second cusp respectively.

3. The method of claim 1, wherein the first cusp is a right semilunar cusp and the second cusp is a posterior semilunar cusp.

4. The method of claim 1, wherein the first cusp is a left semilunar cusp and the second cusp is a posterior semilunar cusp.

5. The method of claim 1, wherein the first cusp is a right semilunar cusp and the second cusp is a left semilunar cusp.

6. The method of claim 1, wherein the shock wave device further comprises a third elongate body, a third balloon sealably enclosing a portion of the third elongate body, and a third shock wave source coupled to the third elongate body and enclosed within the third balloon, wherein the third balloon is independently inflatable with a liquid.

7. The method of claim 1 further including activating the second shock wave source to apply a shock wave to the second cusp.

8. The method of claim 7, wherein the first and second shock wave sources are activated substantially simultaneously.

9. The method of claim 1 wherein the first and second balloons are inflated simultaneously.

10. The method of claim 1 wherein the first balloon is inflated before the second balloon is inflated.

11. A method for applying shock waves to an aortic valve having a first cusp and a second cusp comprising:
   introducing a shock wave device into a patient's vasculature, the shock wave device comprising a first elongate body, a first balloon sealably enclosing a portion of the first elongate body, a first shock wave source coupled to the first elongate body and enclosed within the first balloon, a second elongate body, a second balloon sealably enclosing a portion of the second elongate body, and a second shock wave source coupled to the second elongate body and enclosed within the second balloon, wherein the first and second balloons are independently inflatable with a liquid;

advancing the shock wave device within the vasculature to the aortic valve;

inflating the first balloon with a liquid, wherein inflating the first balloon causes the first balloon to be aligned within a concave portion of the first cusp facing the aorta;

inflating the second balloon with a liquid, wherein inflating the second balloon causes the second balloon to be aligned within a concave portion of the second cusp facing the aorta;

thereafter, deflating the second balloon to permit increased blood flow through the aortic valve;

thereafter activating the first shock wave source to apply a shock wave to the first cusp;

after activating the first shock wave source, reinflating the second balloon with a liquid and deflating the first balloon; and thereafter activating the second shock wave source to apply a shock wave to the second cusp.

12. The method of claim 11 wherein the first and second balloons are initially inflated simultaneously.

13. The method of claim 11 wherein one of the first and second balloons is initially inflated before the other balloon is initially inflated.

* * * * *